US010346751B2

(12) United States Patent
Agarwal et al.

(10) Patent No.: US 10,346,751 B2
(45) Date of Patent: *Jul. 9, 2019

(54) EXTRACTION OF INFERENCE RULES FROM HETEROGENEOUS GRAPHS

(71) Applicant: International Business Machines Corporation, Armonk, NY (US)

(72) Inventors: Apoorv Agarwal, New York, NY (US); Kenneth J. Barker, Mahopac, NY (US); Jennifer Chu-Carroll, Dobbs Ferry, NY (US); Aditya A. Kalyanpur, Westwood, NJ (US); Christopher A. Welty, Flushing, NY (US); Wlodek W. Zadrozny, Charlotte, NC (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 421 days.

This patent is subject to a terminal disclaimer.

(21) Appl. No.: 14/485,942

(22) Filed: Sep. 15, 2014

(65) Prior Publication Data

US 2016/0078343 A1    Mar. 17, 2016

(51) Int. Cl.
*G06N 20/00* (2019.01)
*G06N 5/02* (2006.01)
(Continued)

(52) U.S. Cl.
CPC ......... *G06N 5/025* (2013.01); *G06F 16/9024* (2019.01); *G06F 19/00* (2013.01); *G16H 50/70* (2018.01); *G06N 20/00* (2019.01)

(58) Field of Classification Search
None
See application file for complete search history.

(56) References Cited

U.S. PATENT DOCUMENTS 8,117,135 B2   2/2012   Hong et al.
8,214,401 B2   7/2012   Rao et al.
(Continued)

FOREIGN PATENT DOCUMENTS

EP   1577810   9/2005

OTHER PUBLICATIONS

Berant, J. et al., "Global learning of typed entailment rules." Proc. of 49th Annual Meeting of the Association for Computational Linguistics: Human Language Technologies. vol. 1 (2011) 10 pp.*
(Continued)

*Primary Examiner* — Luis A Sitiriche
*Assistant Examiner* — Brian M Smith
(74) *Attorney, Agent, or Firm* — Cantor Colburn LLP; Will Stock

(57) ABSTRACT

According to an aspect, a heterogeneous graph in a data store is accessed. The heterogeneous graph includes a plurality of nodes having a plurality of node types. The nodes are connected by edges having a plurality of relation types. One or more intermediary graphs are created based on the heterogeneous graph. The intermediary graphs include intermediary nodes that are the relation types of the edges of the heterogeneous graph and include intermediary links between the intermediary nodes based on shared instances of the nodes between relation types in the heterogeneous graph. The intermediary graphs are traversed to find sets of relations based on intermediary links according to a template. An inference rule is extracted from the heterogeneous graph based on finding sets of relations in the intermediary graphs. The inference rule defines an inferred relation type between at least two of the nodes of the heterogeneous graph.

12 Claims, 8 Drawing Sheets

(51) Int. Cl.
*G06F 16/901* (2019.01)
*G16H 50/70* (2018.01)
*G06F 19/00* (2018.01)

(56) References Cited

U.S. PATENT DOCUMENTS 8,285,748 B2 10/2012 Thomas et al.
2008/0005175 A1 1/2008 Bourke et al.
2012/0215733 A1 8/2012 Breiter et al.

OTHER PUBLICATIONS

Raghavan, S. & Mooney, R., "Online inference-rule learning from natural-language extractions" AAAI Workshop: Statistical Relational Artificial Intelligence (Jul. 2013) 7 pp.*

Dinh, Q-T. et al., "Generative structure learning for Markov logic networks based on graph of predicates" Proc. of the 22nd Intl. Joint Conf. on Artificial Intelligence (2011) vol. 22, No. 1. pp. 1249-1254.*

Beyersdorff, O. et al., "Edges as Nodes—a New Approach to Timetable Information" Workshop on Algorithmic Approaches for Transportation Modeling, Optimization, and Systems (ATMOS 2009) 13 pp.*

Fan, J. et al., "Automatic knowledge extraction from documents," IBM Journal of Research and Development, vol. 3, No. 4 (May-Jun. 2012) 10 pp.*

Mochol, "The Methodology for Finding Suitable Ontology Matching Approaches" Ph.D. Thesis, Free University of Berlin, Berlin, Jan. 2009, 235 pages.

D. Zhou, et al., "Co-Ranking Authors and Documents in a Heterogeneous Network," Seventh IEEE International Conference on Data Mining, Oct. 2007, 6 pages.

V. Nebot, et al., "DIDO: a Disease-Determinants Ontology from Web Sources" WWW, '11, Mar. 28-Apr. 1, 2011, India, ACM 978-1-4503-0637-9/11/03, 4 pages.

R. Berlanga, et al., "Exploring and linking biomedical resources through multidimensional semantic spaces," This article is part of the supplement: Semantic Web Applications and Tools for Life Sciences (SWAT4LS) Dec. 2010, 15 pags.

A. Agrawal, et al., "Graph Transformations on Domain-Specific Models" Journal on Software and Systems Modeling, Nov. 2003, 43 pages.

* cited by examiner

EXTRACTION OF INFERENCE RULES FROM HETEROGENEOUS GRAPHS

BACKGROUND

The present disclosure relates generally to inference rule extraction, and more specifically, to extraction of inference rules from heterogeneous graphs.

Information extracted from literature can be summarized either manually or automatically in networks or graphs that define relations between nodes representing various elements. A heterogeneous graph may include several node types and many relation types defined between nodes of the heterogeneous graph. Human users may examine the contents of a heterogeneous graph and attempt to extract knowledge by looking for patterns in relationships between various node types and relation types. However, looking at a heterogeneous graph in a visual interface to infer rules from the heterogeneous graph can be challenging where semantic meaning of relations is not available. Additionally, in a very large graph that includes millions of nodes and edges that define relations between the nodes, it is impractical for a human to extract all inferable rules from the graph.

SUMMARY

Embodiments include a system and computer program product for inference rule extraction from a heterogeneous graph. A heterogeneous graph in a data store is accessed. The heterogeneous graph includes a plurality of nodes having a plurality of node types. The nodes are connected by edges having a plurality of relation types. One or more intermediary graphs are created based on the heterogeneous graph. The one or more intermediary graphs include intermediary nodes that are the relation types of the edges of the heterogeneous graph and further include intermediary links between the intermediary nodes based on shared instances of the nodes between the relation types in the heterogeneous graph. The one or more intermediary graphs are traversed to find sets of relations based on the intermediary links according to a template. An inference rule is extracted from the heterogeneous graph based on finding the sets of relations in the one or more intermediary graphs. The inference rule defines an inferred relation type between at least two of the nodes of the heterogeneous graph.

Additional features and advantages are realized through the techniques of the present disclosure. Other embodiments and aspects of the disclosure are described in detail herein. For a better understanding of the disclosure with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Embodiments disclosed herein relate to inference rule extraction from a heterogeneous graph. As used herein, the term "semantic relations" refers to relationships between concepts or meanings Examples related to the medical field are described herein; however, embodiments are not limited to applications in the medical field. Embodiments can be utilized by any application that uses a heterogeneous graph from which inference rules can be extracted to support data analysis and knowledge extraction, including, but not limited to: troubleshooting and repair (e.g., to facilitate diagnostic analysis of a system or component) and a general question-answer (QA) system.

As one example, in the medical domain, a vast number of knowledge sources and ontologies exist. Such information is also growing and changing extremely quickly, making the information difficult for people to read, process, and remember. The combination of recent developments in information extraction and the availability of unparalleled medical resources thus offer an opportunity to develop new techniques to help healthcare professionals overcome the cognitive challenges they may face in clinical decision making. The medical domain has a vast amount of literature found in textbooks, encyclopedias, guidelines, electronic medical records, and many other sources. The amount of data is also growing at an extremely high speed. Substantial understanding of the medical domain has already been included in the Unified Medical Language System® (UMLS) knowledge base (KB), which includes medical concepts, relations, and definitions. The UMLS KB is a compendium of many controlled vocabularies in the biomedical sciences and may be viewed as a comprehensive thesaurus and ontology of biomedical concepts. It provides a mapping structure among these vocabularies and thus allows translation among the various terminology systems. The 2013 version of the UMLS KB contains information about more than 3 million concepts from over 160 source vocabularies.

Figure 1:
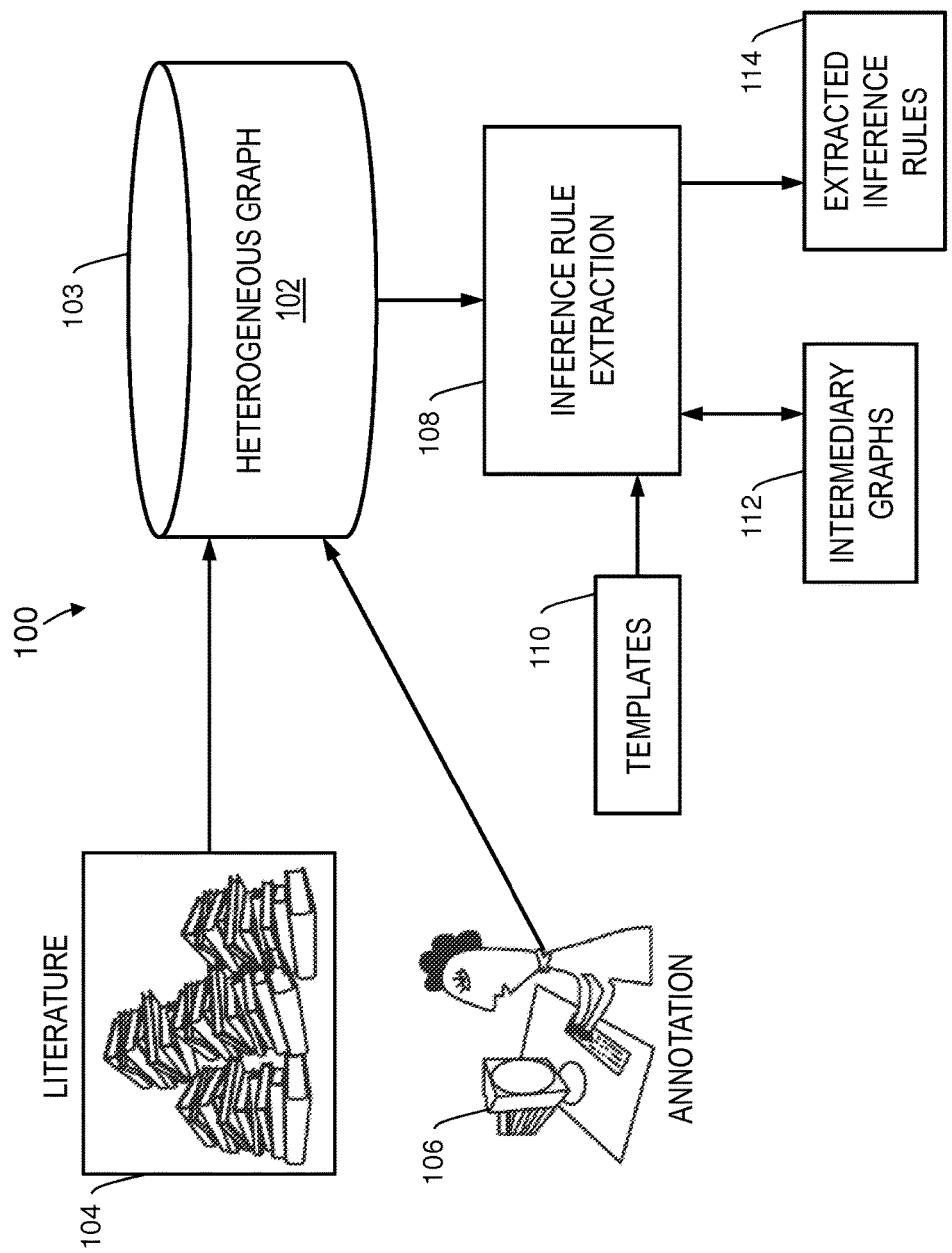
FIG. 1 depicts a block diagram of a system for inference rule extraction in accordance with an embodiment.

FIG. 1 depicts a block diagram of a system 100 for inference rule extraction in accordance with an embodiment. One or more instance of a heterogeneous graph 102 can be constructed based on literature 104 by an automated or manual process and stored in a data store 103. The data store 103 can be a memory device or subsystem, such as a computer memory system, and may be distributed between multiple physical locations or stored at a single location. The literature 104 can include a body of documents, journals, manuals, studies, and the like which describe information. Natural language processing and semantic relation extraction can be used to convert information in the literature 104 into the heterogeneous graph 102. Annotation 106 can be performed on the heterogeneous graph 102 to add or modify semantic relations. Alternatively, Annotation 106 can be used to manually create a heterogeneous graph without relying on automatic techniques. The UMLS KB is one example of a manually constructed heterogeneous graph that includes several million nodes, such as diseases, treatments, and symptoms, as well as hundreds of semantic relation types defined between nodes. As the size of the heterogeneous graph 102 grows, it may be too unwieldy to manually inspect thousands or millions of concepts captured in the heterogeneous graph 102 to discover and infer rules captured therein.

As one example, if a brute force approach is taken manually or by a computer implemented process to discover all rules pertaining to one node, where a total number of n nodes exist in a graph and the out-degree of each node is T (i.e., number of relation types), overall complexity of the inspection process for each node would be $O(n^2*T^3)$ in big-O notation, i.e., order of the growth rate of the function. This is because for each node, rules can be mined that pertain to two of (n−1) other nodes. Selection can be done in (n−1)C(2) ways, where C is a node about which rules are sought. To traverse all the directional rules between three nodes, complexity is $O(T^3)$, and hence the complexity for all n nodes is $O(n^3*T^3)$. Exemplary embodiments improve computing system functionality by reducing computational complexity to $O(n^2+T^3)$ to infer all rules. Larger graph sizes would see larger degrees of computational improvement, thus improving computer system functionality by reducing required time to extract all rules that can be inferred from a heterogeneous graph and increasing processing resource availability for other tasks.

In the example of FIG. 1, inference rule extraction 108 accesses one or more templates 110 to discover a rule pattern for a rule to be inferred and extracted from the heterogeneous graph 102. An example of a rule pattern in the templates 110 is: "If A relation_x B and B relation_y C then A relation_z C", where A, B, and C are node types and relation_x, relation_y, and relation_z are relation types. An inference rule can define an inferred relation type between at least two of the nodes of the heterogeneous graph 102. The inference rule extraction 108 can access the heterogeneous graph 102 in the data store 103. To infer such a rule for particular instances of nodes and relations within the heterogeneous graph 102, the inference rule extraction 108 creates one or more intermediary graphs 112. The intermediary graphs 112 include intermediary nodes that are relation types of the edges of the heterogeneous graph 102. The intermediary graphs 112 also include intermediary links between the intermediary nodes based on shared instances of nodes between the relation types in the heterogeneous graph 102. The intermediary graphs 112 may be traversed to find sets of relations based on the intermediary links according to a rule pattern of the templates 110. An inference rule can be extracted from the heterogeneous graph 102 and stored in extracted inference rules 114 based on finding the sets of relations in the intermediary graphs 112.

As one example, the intermediary graphs 112 can include a source intermediary graph having intermediary nodes connected with undirected links as intermediary links. The undirected links may be based on the relation types of the intermediary nodes sharing a common source node in the heterogeneous graph 102. The intermediary graphs 112 can also include a target intermediary graph having the intermediary nodes connected with undirected links as the intermediary links, where the undirected links are based on the relation types of the intermediary nodes sharing a common target node in the heterogeneous graph 102. The intermediary graphs 112 may also include a target-source intermediary graph having the intermediary nodes connected with directed links as the intermediary links. The directed links can be based on the relation types of the intermediary nodes having a source node that is a target node of another relation type in the heterogeneous graph 102.

Figure 2:
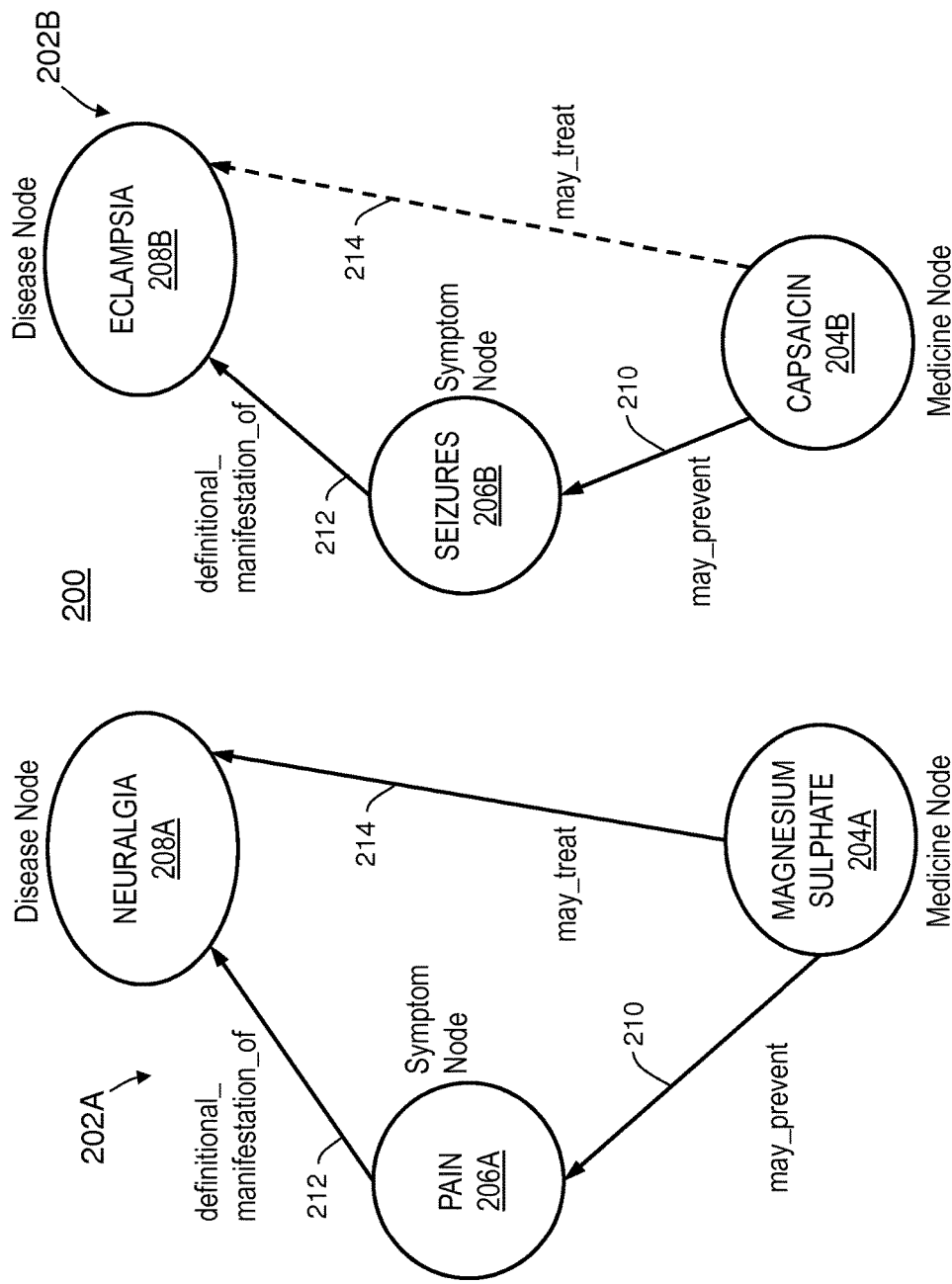
FIG. 2 depicts an example of a heterogeneous graph in accordance with an embodiment.

FIG. 2 depicts an example of a heterogeneous graph 200 in accordance with an embodiment. The heterogeneous graph 200 is an example of a portion of the heterogeneous graph 102 of FIG. 1. The heterogeneous graph 200 includes multiple groups 202A, 202B that have common relations, as well as other groups (not depicted). Group 202A includes a medicine node 204A that has a value of "magnesium sulphate", a symptom node 206A that has a value of "pain", and a disease node 208A that has a value of "neuralgia", where the medicine node 204A, symptom node 206A, and disease node 208A are examples of different node types. Group 202A also includes a number of relations defined between the node types. In the example of FIG. 2, from medicine node 204A to symptom node 206A, a may_prevent relation 210 is defined as an edge. From symptom node 206A to disease node 208A, a definitional_manifestion_of relation 212 is defined as an edge. A may_treat relation 214 is defined as an edge between the medicine node 204A and disease node 208A. The may_prevent relation 210, definitional_manifestion of relation 212, and may_treat relation 214 are examples of different relation types that are edges in the heterogeneous graph 200.

The group 202B includes a medicine node 204B that has a value of "capsaicin", a symptom node 206B that has a value of "seizures", and a disease node 208B that has a value of "eclampsia", where the medicine node 204B, symptom node 206B, and disease node 208B are examples of different node types. Group 202B also includes a number of relations defined as edges between the node types. In the example of FIG. 2, from medicine node 204B to symptom node 206B, a may_prevent relation 210 relation is defined as an edge. From symptom node 206B to disease node 208B, a definitional_manifestion_of relation 212 is defined as an edge. In an exemplary embodiment, a relation between medicine node 204B and disease node 208B may not be defined but can be inferred as a may_treat relation 214 as further described herein.

Figure 3A:
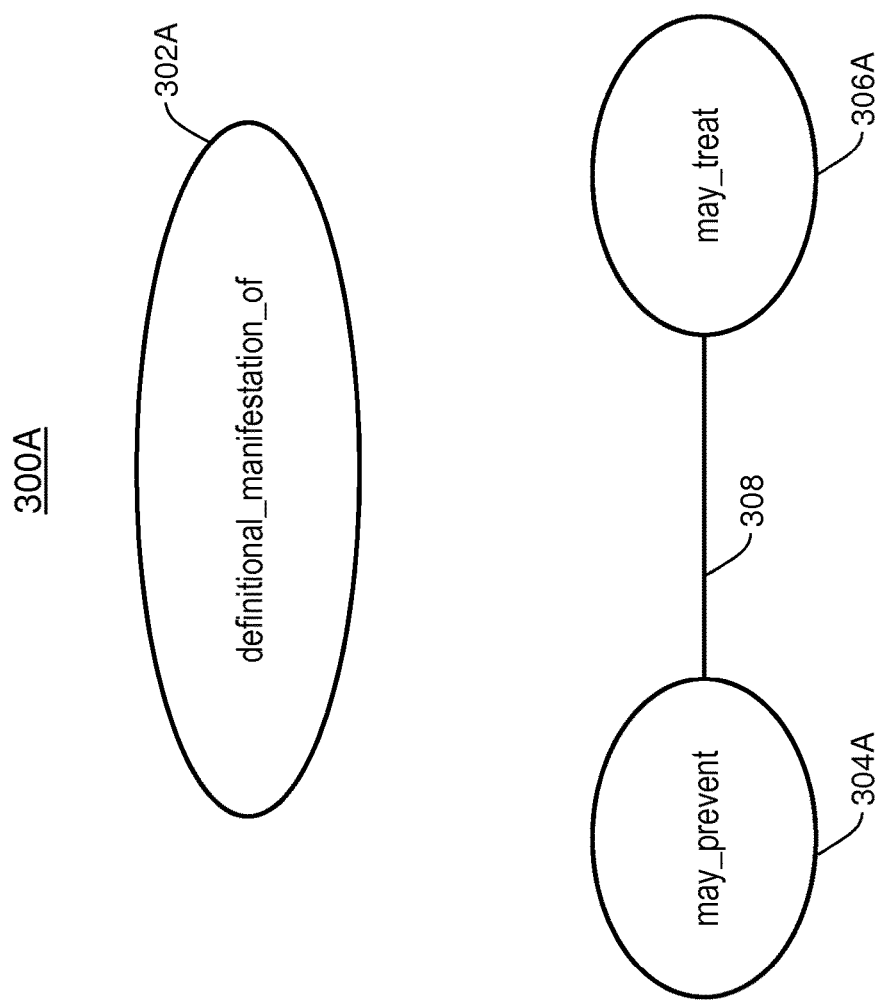
FIG. 3A depicts a source intermediary graph as an intermediary graph in accordance with an embodiment.
Figure 3B:
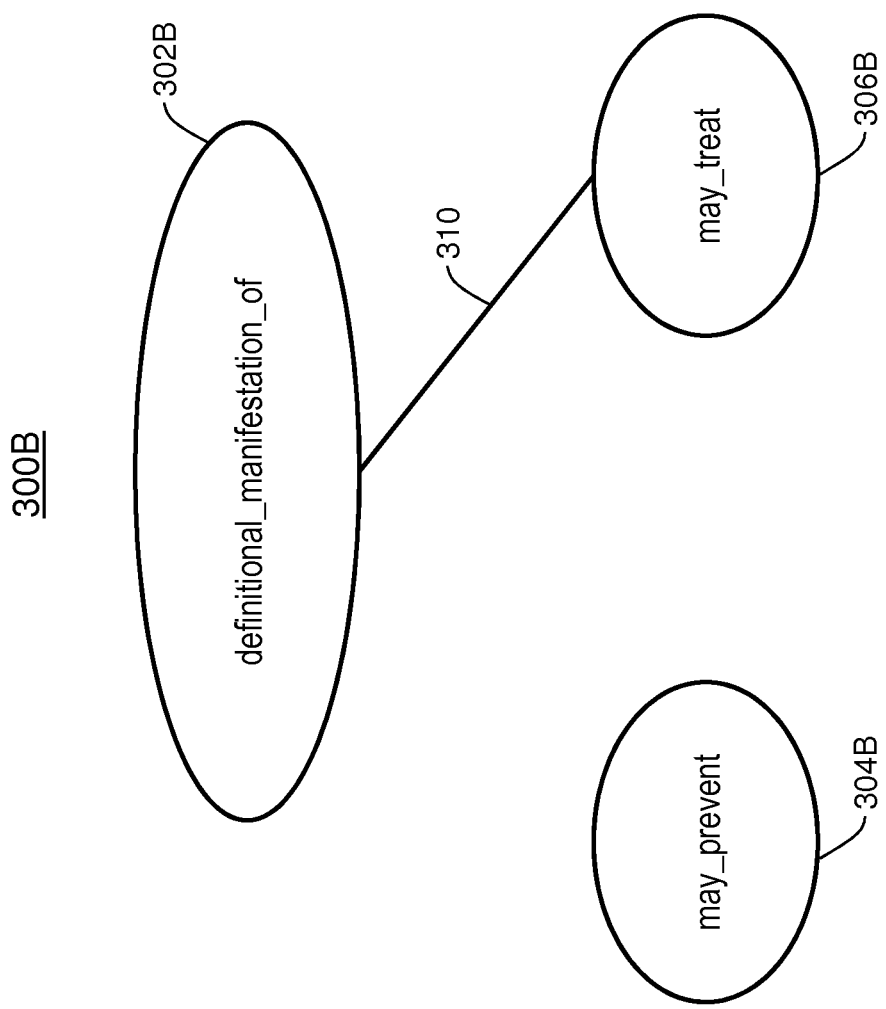
FIG. 3B depicts a target intermediary graph as an intermediary graph in accordance with an embodiment.
Figure 3C:
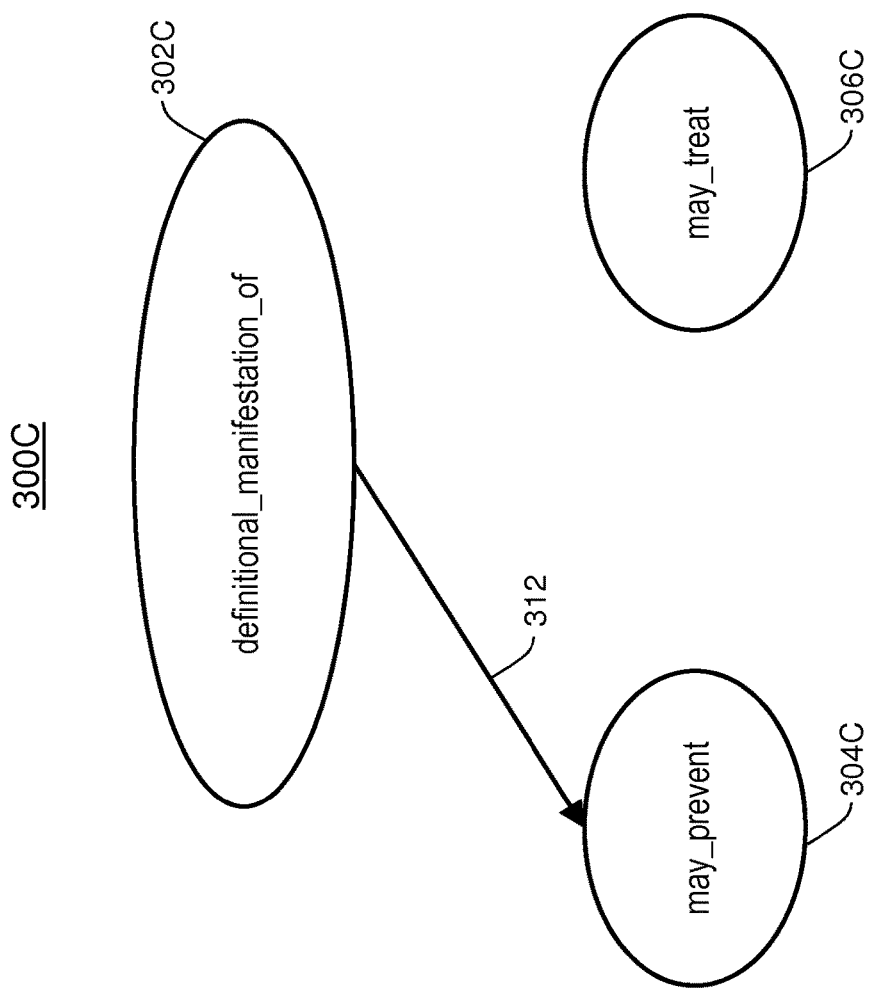
FIG. 3C depicts a target-source intermediary graph as an intermediary graph in accordance with an embodiment.

Upon accessing the heterogeneous graph 200 of FIG. 2, the inference rule extraction 108 of FIG. 1 can create the intermediary graphs 112 of FIG. 1 including a source intermediary graph 300A of FIG. 3A, a target intermediary graph 300B of FIG. 3B, and a target-source intermediary graph 300C of FIG. 3C.

The source intermediary graph 300A of FIG. 3A includes an intermediary node 302A that has a value of "definitional_manifestation_of" as a relation type of the edge: definitional_manifestion_of relation 212 of FIG. 2. The source intermediary graph 300A also includes an intermediary node 304A that has a value of "may_prevent" as a relation type of the edge: may_prevent relation 210 of FIG. 2. The source intermediary graph 300A further includes an intermediary node 306A that has a value of "may_treat" as a relation type of the edge: may_treat relation 214 of FIG. 2. The source intermediary graph 300A can connect intermediary nodes 304A and 306A with an undirected link 308 as an intermediary link. The intermediary nodes 304A and 306A are relation types that share a common source node in the heterogeneous graph 200 of FIG. 2. For example, medicine node 204A is a common source node of the may_prevent relation 210 and the may_treat relation 214 of FIG. 2.

In general terms, the source intermediary graph 300A is defined as follows: an intermediary link exists between two intermediary nodes (e.g., relation_x and relation_y) if the source nodes for those relations are sufficiently similar. As an example, a set of source nodes (S) of relation_x and a set of source nodes (S) of relation_y can be considered sufficiently similar if the Jaccard value (J) between S(relation_x) and S(relation_y) is non-zero, i.e., J(S(relation_x), S(relation_y))>0. A Jaccard value measures the similarity between two sets and is defined as the size of the intersection of the sets divided by the size of the union of the sets.

FIG. 3B depicts the target intermediary graph 300B as one of the intermediary graphs 112 of FIG. 1 in accordance with an embodiment. The target intermediary graph 300B includes an intermediary node 302B that has a value of "definitional_manifestation_of" as a relation type of the edge: definitional_manifestion_of relation 212 of FIG. 2. The target intermediary graph 300B also includes an intermediary node 304B that has a value of "may_prevent" as a relation type of the edge: may_prevent relation 210 of FIG. 2. The target intermediary graph 300B further includes an intermediary node 306B that has a value of "may_treat" as a relation type of the edge: may_treat relation 214 of FIG. 2. The target intermediary graph 300B can connect intermediary nodes 302B and 306B with an undirected link 310 as an intermediary link. The intermediary nodes 302B and 306B are relation types that share a common target node in the heterogeneous graph 200 of FIG. 2. For example, disease node 208A is a common target node of the definitional_manifestion_of relation 212 and the may_treat relation 214 of FIG. 2.

In general terms, the target intermediary graph 300B is defined as follows: an intermediary link exists between two intermediary nodes (e.g., relation_x and relation_y) if the sets of target nodes for the two relations are sufficiently similar. Again, a set of target nodes (T) of relation_x and a set of target nodes (T) of relation_y can be considered sufficiently similar if the Jaccard value (J) between T(relation_x) and T(relation_y) is non-zero, i.e., J(T(relation_x), T(relation_y))>0.

FIG. 3C depicts the target-source intermediary graph 300C as one of the intermediary graphs 112 of FIG. 1 in accordance with an embodiment. The target-source intermediary graph 300C includes an intermediary node 302C that has a value of "definitional_manifestation_of" as a relation type of the edge: definitional_manifestion_of relation 212 of FIG. 2. The target-source intermediary graph 300C also includes an intermediary node 304C that has a value of "may_prevent" as a relation type of the edge: may_prevent relation 210 of FIG. 2. The target-source intermediary graph 300C further includes an intermediary node 306C that has a value of "may_treat" as a relation type of the edge: may_treat relation 214 of FIG. 2. The target-source intermediary graph 300C can connect intermediary nodes 302C and 304C with a directed link 312 as an intermediary link from intermediary node 302C to intermediary node 304C. The intermediary nodes 302C and 304C are relation types such that the source node of one is the target node of the other in the heterogeneous graph 200 of FIG. 2. For example, symptom node 206A is a source node of the definitional_manifestion_of relation 212 and is a target node with respect to the may_prevent relation 210 of FIG. 2.

In general terms, the target-source intermediary graph 300C is defined as follows: an intermediary link exists between two intermediary nodes (e.g., relation_x and relation_y) if the set of target nodes (T) of relation_x and the set of source nodes(S) of relation_y are sufficiently similar. The Jaccard value (J) between T(relation_x) and S(relation_y) can be used to measure similarity. In this graph, unlike the source intermediary graph 300A and the target intermediary graph 300B of FIGS. 3A and 3B, edges are directional, pointing from relation_x to relation_y.

Using the combination of the source intermediary graph 300A, the target intermediary graph 300B, and the target-source intermediary graph 300C, one or more of the extracted inference rules 114 can be extracted. As one example, for each edge, (r_1, r_2), in the target-source intermediary graph 300C, a set of relations R_3_1 can be found such that (r_1, r_3_1) exists in the source intermediary graph 300A and a set of relations R_3_2 can be found such that (r_2, r_3_2) exists in the target intermediary graph 300B. A set of relations R_3 equals R_3_1 intersected with R_3_2. This results in mining inference rules matching a rule pattern "if A r_1 B and B r_2 C then A r_3 C" from the templates 110 of FIG. 1.

As a generalized example, consider an inference rule (a--r_1--b, b--r_2--c, a--r_3--c). Set S denotes a set of source nodes for a relation type, and set T denotes a set of target nodes for a relation type. Since this inference rule exists, T(r_1)∩S(r_2) is non-empty (i.e., it has element b). S(r_1)∩S(r_3) is non-empty (i.e., it has element a). T(r_2)∩T(r_3) is non-empty (i.e., it has element c). Thus, an inference rule can be found.

By applying the inference rule extraction 108 of FIG. 1 to group 202A of FIG. 2, the intermediary graphs 112 of FIG. 1 can include the source intermediary graph 300A of FIG. 3A, the target intermediary graph 300B of FIG. 3B, and the target-source intermediary graph 300C of FIG. 3C. Where the templates 110 of FIG. 1 include the rule pattern "if A r_1 B and B r_2 C then A r_3 C", the extracted inference rules 114 of FIG. 1 for group 202A of FIG. 2 can include "if magnesium sulphate may prevent pain and pain is a definitional_manifestation_of neuralgia then magnesium sulphate may treat neuralgia". This can be generalized to an inferred rule that if a medicine node has a may_prevent relation to a symptom node and the symptom node has a definitional_manifestation_of relation to a disease node, then the medicine node should also have a may_treat relation to the disease node. If may_treat relation 214 is missing or not labeled for group 202B of FIG. 2, a may_treat relation 214 can be inferred between medicine node 204B (FIG. 2) and disease node 208B (FIG. 2) based on the inferred rule extracted from group 202A of FIG. 2. Thus, it can be inferred that "if capsaicin may prevent seizures and seizures are a definitional_manifestation_of eclampsia then capsaicin may treat eclampsia".

Figure 4:
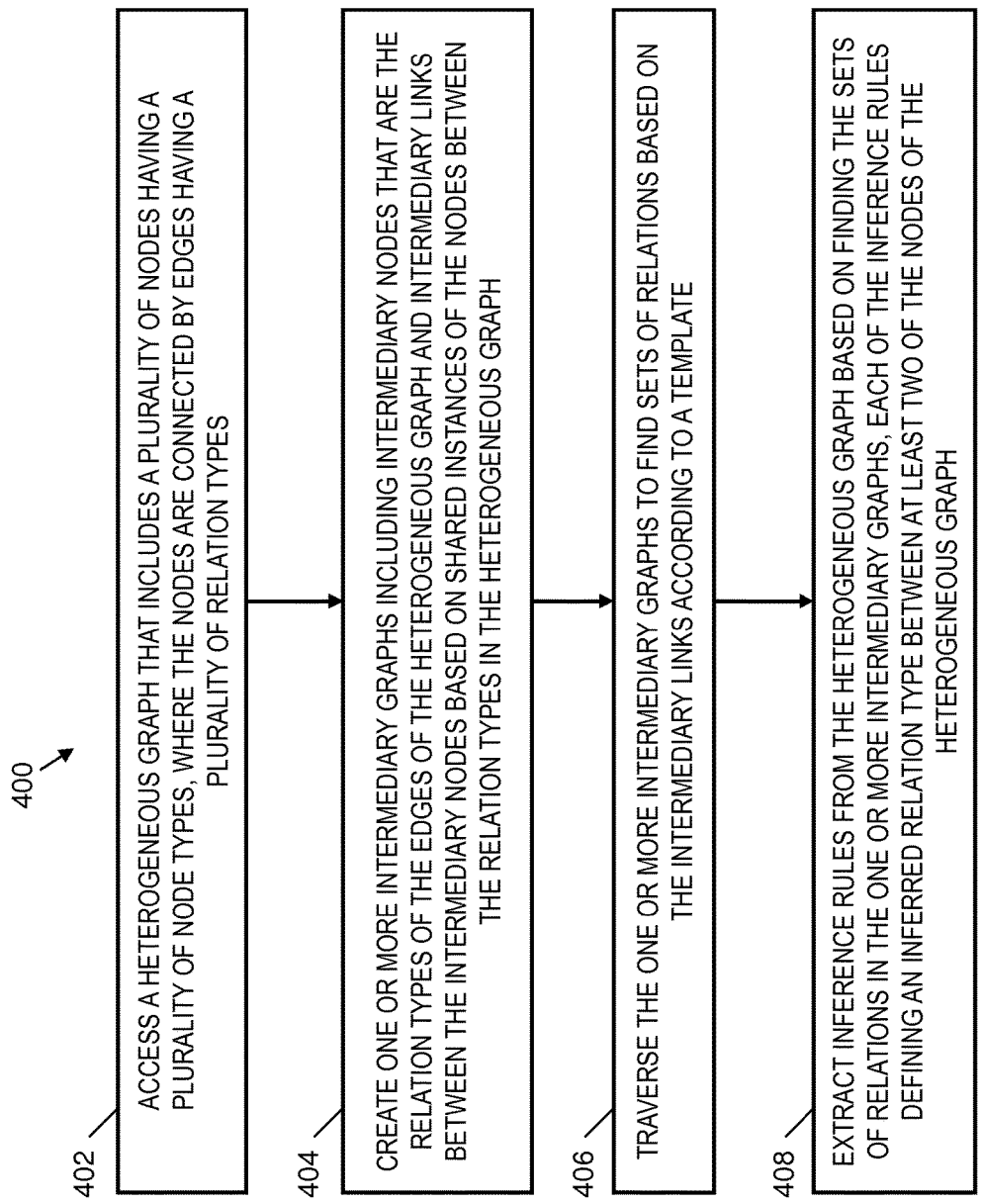
FIG. 4 depicts a process flow for inference rule extraction from a heterogeneous graph in accordance with an embodiment.

FIG. 4 depicts a process flow 400 for inference rule extraction from a heterogeneous graph in accordance with an embodiment. The process flow 400 provides an example of a method for inference rule extraction. For purposes of explanation, the process flow 400 is described in terms of the examples of FIGS. 1-3C but can be implemented on various system configurations, including heterogeneous graphs with millions of nodes resulting in millions of extracted inference rules.

At block 402, a heterogeneous graph in a data store is accessed, such as the heterogeneous graph 102 in data store 103 of FIG. 1. The heterogeneous graph can include a plurality of nodes having a plurality of node types. The nodes are connected by edges having a plurality of relation types, as in the example of FIG. 2.

At block 404, one or more intermediary graphs are created based on the heterogeneous graph, such as intermediary graphs 112 of FIG. 1 and intermediary graphs 300A-300C of FIGS. 3A-3C. The one or more intermediary graphs include intermediary nodes that are the relation types of the edges of the heterogeneous graph. The one or more intermediary graphs also include intermediary links between the intermediary nodes based on shared instances of the nodes between the relation types in the heterogeneous graph. A source intermediary graph, such as source intermediary graph 300A of FIG. 3, can be created as one of the intermediary graphs by connecting intermediary nodes with undirected links as the intermediary links, where the undirected links are based on the relation types of the intermediary nodes sharing a common source node in the heterogeneous graph. A target intermediary graph, such as target intermediary graph 300B of FIG. 3B, can be created as one of the intermediary graphs by connecting intermediary nodes with undirected links as the intermediary links, where the undirected links are based on the relation types of the intermediary nodes sharing a common target node in the heterogeneous graph. A target-source intermediary graph, such as target-source intermediary graph 300C of FIG. 3, can be created as one of the intermediary graphs by connecting intermediary nodes with directed links as the intermediary links, where the directed links are based on the relation types of the intermediary nodes having a source node that is a target node of another relation type in the heterogeneous graph.

At block 406, the one or more intermediary graphs are traversed to find sets of relations based on the intermediary links according to a template. As an example, for each intermediary link between a first relation type and a second relation type in the target-source intermediary graph, the source intermediary graph can be examined to find a first set of relations in the source intermediary graph associated with the first relation type. The target intermediary graph can be examined to find a second set of relations in the target intermediary graph associated with the second relation type. An intersection between the first set of relations and the second set of relations can be determined.

At block 408, an inference rule is extracted from the heterogeneous graph based on finding the sets of relations in the one or more intermediary graphs. The inference rule defines an inferred relation type between at least two of the nodes of the heterogeneous graph. Inference rules can be stored in the extracted inference rules 114 of FIG. 1 for use by other processes that may apply generalized versions of the extracted inference rules 114 to identify missing relations, create higher level inferences, or perform other types of rule-based analysis. The heterogeneous graph can be traversed to extract all inference rules that are inferable from the heterogeneous graph according to the template, which may be one of the templates 110 of FIG. 1. A template may define a rule pattern, such as: three node types having three relation types between the three node types.

Figure 5:
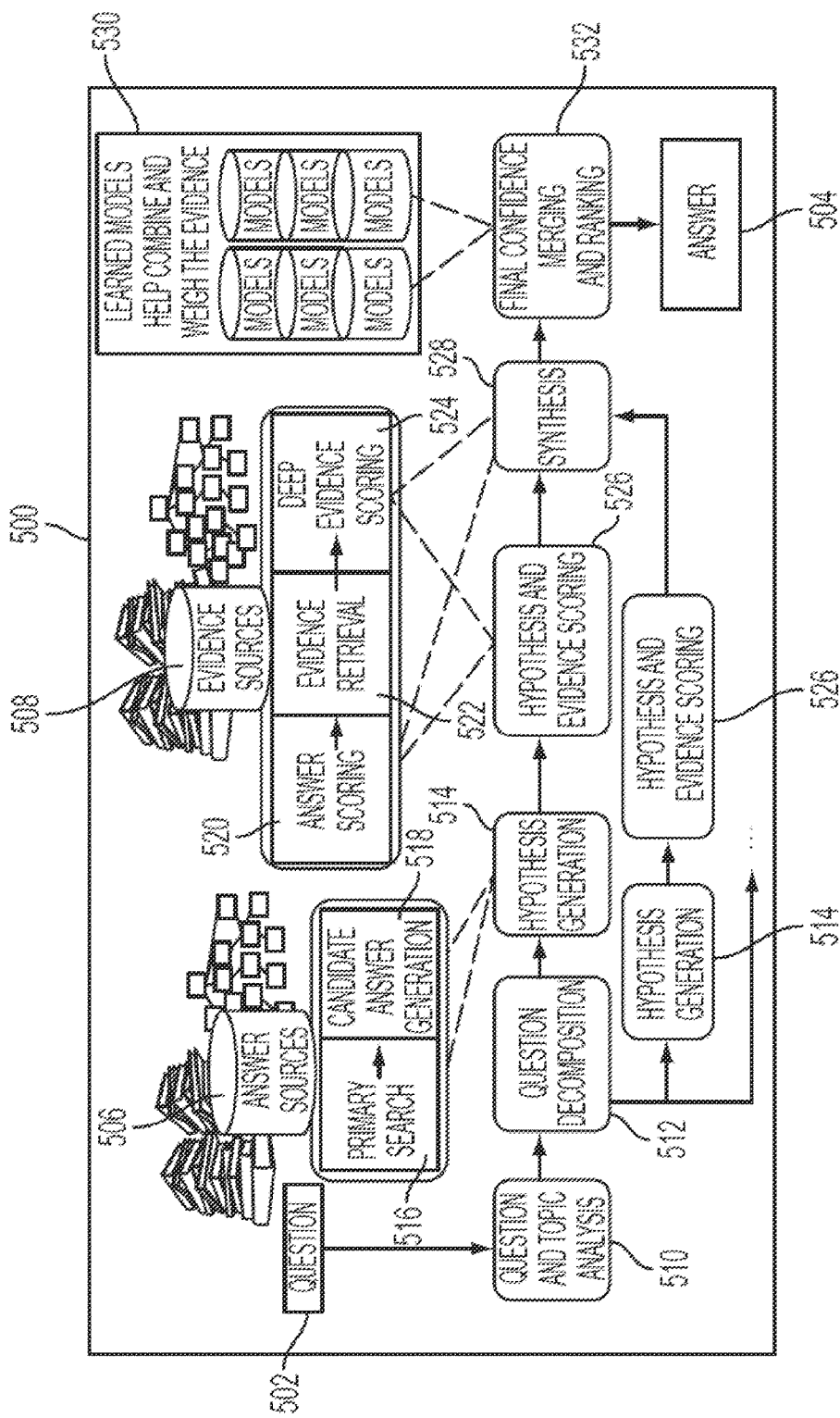
FIG. 5 depicts a high-level block diagram of a question-answer (QA) framework where embodiments of inference rule extraction can be implemented in accordance with an embodiment.

Turning now to FIG. 5, a high-level block diagram of a question-answer (QA) framework 500 where embodiments described herein can be utilized is generally shown.

The QA framework 500 can be implemented to generate a ranked list of answers 504 (and a confidence level associated with each answer) to a given question 502. In an embodiment, general principles implemented by the framework 500 to generate answers 504 to questions 502 include massive parallelism, the use of many experts, pervasive confidence estimation, and the integration of shallow and deep knowledge. In an embodiment, the QA framework 500 shown in FIG. 5 is implemented by the Watson™ product from IBM.

The QA framework 500 shown in FIG. 5 defines various stages of analysis in a processing pipeline. In an embodiment, each stage admits multiple implementations that can produce alternative results. At each stage, alternatives can be independently pursued as part of a massively parallel computation. Embodiments of the framework 500 don't assume that any component perfectly understands the question 502 and can just look up the right answer 504 in a database. Rather, many candidate answers can be proposed by searching many different resources, on the basis of different interpretations of the question (e.g., based on a category of the question.) A commitment to any one answer is deferred while more and more evidence is gathered and analyzed for each answer and each alternative path through the system.

As shown in FIG. 5, the question and topic analysis 510 is performed and used in question decomposition 512. Hypotheses are generated by the hypothesis generation block 514 which uses input from the question decomposition 512, as well as data obtained via a primary search 516 through the answer sources 506 and candidate answer generation 518 to generate several hypotheses. Hypothesis and evidence scoring 526 is then performed for each hypothesis using evidence sources 508 and can include answer scoring 520, evidence retrieval 522 and deep evidence scoring 524.

A synthesis 528 is performed of the results of the multiple hypothesis and evidence scorings 526. Input to the synthesis 528 can include answer scoring 520, evidence retrieval 522, and deep evidence scoring 524. Learned models 530 can then be applied to the results of the synthesis 528 to generate a final confidence merging and ranking 532. A ranked list of answers 504 (and a confidence level associated with each answer) is then output.

Relation extraction plays a key role in information extraction in the QA framework 500 shown in FIG. 5. Embodiments of the inference rule extraction herein can be utilized by the QA framework 500 to improve relation extraction. Embodiments can be utilized, for example, in candidate answer generation 518, where extracted inference rules from the answer sources 506 can be used for potential candidate answer generation. Also, in evidence retrieval 522 and deep evidence scoring 524, extracted inference rules from the evidence sources 508 can be utilized to detect implicit relations across the question and passages.

The framework 500 shown in FIG. 5 can utilize embodiments of the inference rule extraction described herein to create learned models 530 by training statistical machine learning algorithms on prior sets of questions and answers to learn how best to weight each of the hundreds of features relative to one another. These weights can be used at run time to balance all of the features when combining the final scores for candidate answers to new questions 502. In addition, embodiments can be used to generate a KB based on a corpus of data that replaces or supplements commercially available KBs.

Figure 6:
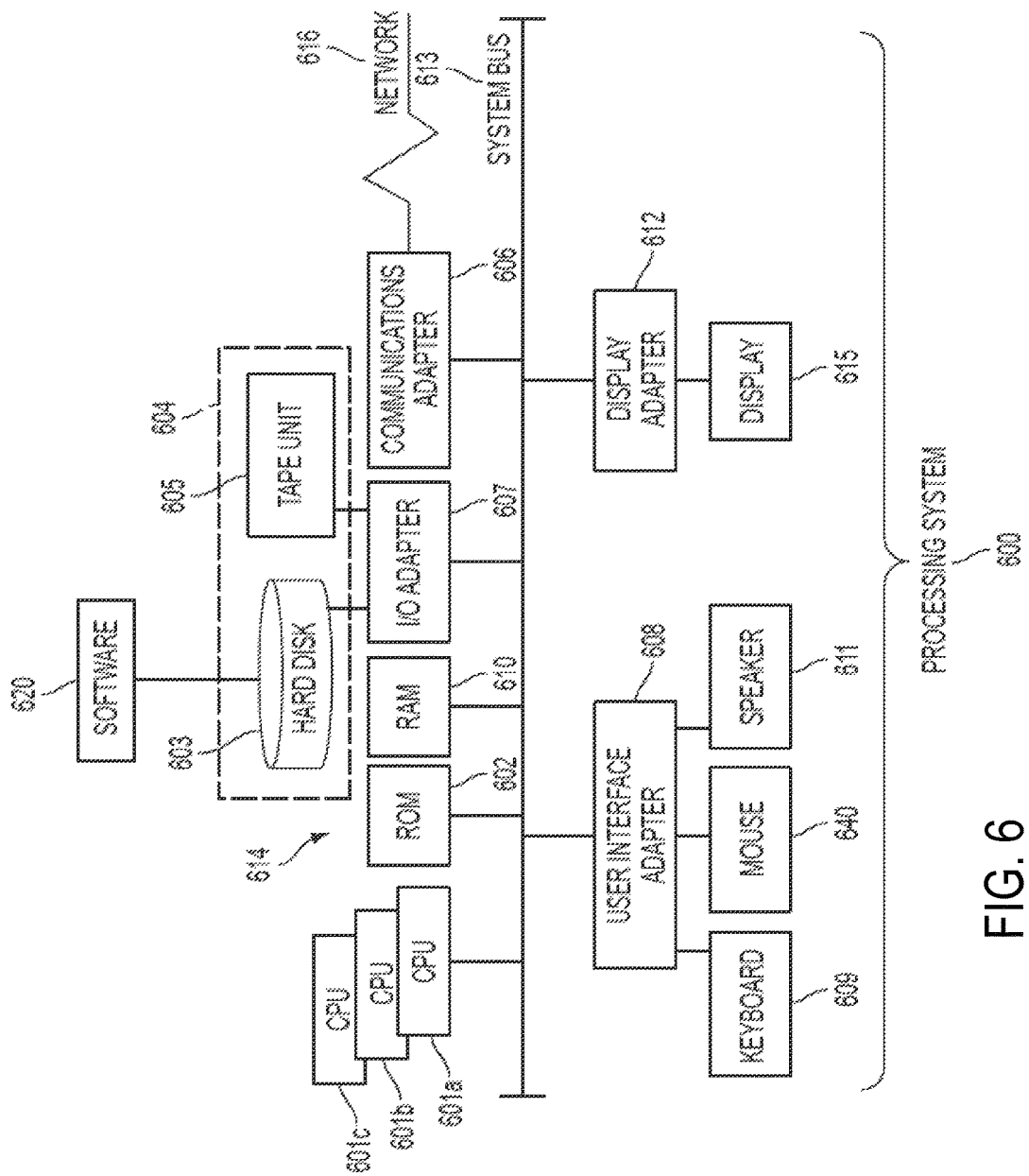
FIG. 6 depicts a processing system in accordance with an embodiment.

Referring now to FIG. 6, there is shown an embodiment of a processing system 600 for implementing the teachings herein. In this embodiment, the processing system 600 has one or more central processing units (processors) 601*a*, 601*b*, 601*c*, etc. (collectively or generically referred to as processor(s) 601). Processors 601, also referred to as processing circuits, are coupled to system memory 614 and various other components via a system bus 613. Read only memory (ROM) 602 is coupled to system bus 613 and may include a basic input/output system (BIOS), which controls certain basic functions of the processing system 600. The system memory 614 can include ROM 602 and random access memory (RAM) 610, which is read-write memory coupled to system bus 613 for use by processors 601.

FIG. 6 further depicts an input/output (I/O) adapter 607 and a network adapter 606 coupled to the system bus 613. I/O adapter 607 may be a small computer system interface (SCSI) adapter that communicates with a hard disk 603 and/or tape storage drive 605 or any other similar component. I/O adapter 607, hard disk 603, and tape storage drive 605 are collectively referred to herein as mass storage 604. Software 620 for execution on processing system 600 may be stored in mass storage 604. The mass storage 604 is an example of a tangible storage medium readable by the processors 601, where the software 620 is stored as instructions for execution by the processors 601 to perform a method, such as the process flow 400 of FIG. 4. Network adapter 606 interconnects system bus 613 with an outside network 616 enabling processing system 600 to communicate with other such systems. A screen (e.g., a display monitor) 615 is connected to system bus 613 by display adapter 612, which may include a graphics controller to improve the performance of graphics intensive applications and a video controller. In one embodiment, adapters 607, 606, and 612 may be connected to one or more I/O buses that are connected to system bus 613 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 613 via user interface adapter 608 and display adapter 612. A keyboard 609, mouse 640, and speaker 611 can be interconnected to system bus 613 via user interface adapter 608, which may include, for example, a Super I/O chip integrating multiple device adapters into a single integrated circuit.

Thus, as configured in FIG. 6, processing system 600 includes processing capability in the form of processors 601, and, storage capability including system memory 614 and mass storage 604, input means such as keyboard 609 and mouse 640, and output capability including speaker 611 and display 615. In one embodiment, a portion of system memory 614 and mass storage 604 collectively store an operating system such as the AIX® operating system from IBM Corporation to coordinate the functions of the various components shown in FIG. 6.

Technical effects and benefits include inference rule extraction from a heterogeneous graph using intermediary graphs to increase processing efficiency and reduce latency.

The present invention may be a system, a method, and/or a computer program product. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer program product comprising:
a tangible storage medium readable by one or more processing circuits and storing instructions for execution by the one or more processing circuits to perform a method comprising:
accessing a heterogeneous graph in a data store, the heterogeneous graph comprising a plurality of nodes having a plurality of node types, the nodes connected by edges having a plurality of relation types;
creating one or more intermediary graphs based on the heterogeneous graph, the one or more intermediary graphs comprising intermediary nodes that are the relation types of the edges of the heterogeneous graph and further comprising intermediary links between the intermediary nodes based on shared instances of the nodes between the relation types in the heterogeneous graph, wherein creating one or more intermediary graphs based on the heterogeneous graph comprises creating a source intermediary graph comprising the intermediary nodes connected with undirected links as the intermediary links, the undirected links based on the relation types of the intermediary nodes sharing a common source node in the heterogeneous graph;
traversing the one or more intermediary graphs to find sets of relations based on the intermediary links according to a template;
extracting inference rules from the heterogeneous graph based on finding the sets of relations in the one or more intermediary graphs, each of the inference rules defining an inferred relation type between at least two of the nodes of the heterogeneous graph in a relation extraction process of a question-answer computer system; and
using the inference rules to perform a question answering process by the question-answer computer system, the question answering process comprising creating a plurality of learned models by training a plurality of statistical machine learning algorithms on a plurality of prior sets of questions and answers to learn a plurality of weights for a plurality of features and using the learned models to apply the weights at run time to balance the features when combining a plurality of final scores for a plurality of candidate answers to one or more new questions.

2. The computer program product of claim 1, wherein the instructions for execution by the one or more processing circuits further comprise:
using one or more of the inference rules extracted from one or more answer sources in generating one or more of the candidate answers.

3. The computer program product of claim 1, wherein creating one or more intermediary graphs further comprises:
creating a target intermediary graph comprising the intermediary nodes connected with undirected links as the intermediary links, the undirected links based on the relation types of the intermediary nodes sharing a common target node in the heterogeneous graph.

4. The computer program product of claim 3, wherein creating one or more intermediary graphs further comprises:
creating a target-source intermediary graph comprising the intermediary nodes connected with directed links as the intermediary links, the directed links based on the relation types of the intermediary nodes having a source node that is a target node of another relation type in the heterogeneous graph.

5. The computer program product of claim 4, further comprising for each intermediary link between a first relation type and a second relation type in the target-source intermediary graph:
   finding a first set of relations in the source intermediary graph associated with the first relation type;
   finding a second set of relations in the target intermediary graph associated with the second relation type; and
   determining an intersection between the first set of relations and the second set of relations.

6. The computer program product of claim 1, wherein the method further comprises:
   traversing the heterogeneous graph to extract all of the inference rules that are inferable from the heterogeneous graph according to the template.

7. The computer program product of claim 6, wherein the template defines a rule pattern as three node types having three relation types between the three node types.

8. A system comprising:
   a memory having computer readable instructions; and
   one or more processors for executing the computer readable instructions, the computer readable instructions including:
   accessing a heterogeneous graph in a data store, the heterogeneous graph comprising a plurality of nodes having a plurality of node types, the nodes connected by edges having a plurality of relation types;
   creating one or more intermediary graphs based on the heterogeneous graph, the one or more intermediary graphs comprising intermediary nodes that are the relation types of the edges of the heterogeneous graph and further comprising intermediary links between the intermediary nodes based on shared instances of the nodes between the relation types in the heterogeneous graph, wherein creating one or more intermediary graphs based on the heterogeneous graph comprises creating a source intermediary graph comprising the intermediary nodes connected with undirected links as the intermediary links, the undirected links based on the relation types of the intermediary nodes sharing a common source node in the heterogeneous graph;
   traversing the one or more intermediary graphs to find sets of relations based on the intermediary links according to a template;
   extracting inference rules from the heterogeneous graph based on finding the sets of relations in the one or more intermediary graphs, each of the inference rules defining an inferred relation type between at least two of the nodes of the heterogeneous graph in a relation extraction process of a question-answer computer system; and
   using the inference rules to perform a question answering process by the question-answer computer system, the question answering process comprising creating a plurality of learned models by training a plurality of statistical machine learning algorithms on a plurality of prior sets of questions and answers to learn a plurality of weights for a plurality of features and using the learned models to apply the weights at run time to balance the features when combining a plurality of final scores for a plurality of candidate answers to one or more new questions.

9. The system of claim 8, wherein the computer readable instructions further comprise:
   using one or more of the inference rules extracted from one or more answer sources in generating one or more of the candidate answers.

10. The system of claim 8, wherein creating one or more intermediary graphs further comprises:
    creating a target intermediary graph comprising the intermediary nodes connected with undirected links as the intermediary links, the undirected links based on the relation types of the intermediary nodes sharing a common target node in the heterogeneous graph.

11. The system of claim 10, wherein creating one or more intermediary graphs further comprises:
    creating a target-source intermediary graph comprising the intermediary nodes connected with directed links as the intermediary links, the directed links based on the relation types of the intermediary nodes having a source node that is a target node of another relation type in the heterogeneous graph.

12. The system of claim 11, further comprising for each intermediary link between a first relation type and a second relation type in the target-source intermediary graph:
    finding a first set of relations in the source intermediary graph associated with the first relation type;
    finding a second set of relations in the target intermediary graph associated with the second relation type; and
    determining an intersection between the first set of relations and the second set of relations.

* * * * *